United States Patent [19]

Katsuno et al.

[11] Patent Number: 5,073,652
[45] Date of Patent: Dec. 17, 1991

[54] PROCESS FOR PREPARING AROMATIC HYDROCARBONS

[75] Inventors: Hisashi Katsuno; Michio Sugimoto, both of Sodegaura, Japan

[73] Assignee: Research Association for Utilization of Light Oil, Tokyo, Japan

[21] Appl. No.: 586,343

[22] Filed: Sep. 21, 1990

[30] Foreign Application Priority Data

Sep. 25, 1989 [JP] Japan .................................. 1-248616

[51] Int. Cl.$^5$ ............................................... C07C 2/52
[52] U.S. Cl. .................................. 585/419; 585/417; 208/139
[58] Field of Search ................. 585/419, 417; 208/139

[56] References Cited

U.S. PATENT DOCUMENTS 4,416,806 11/1983 Bernard et al. ...................... 585/419
4,761,512 8/1988 Katsuno et al. ...................... 585/419

FOREIGN PATENT DOCUMENTS 0201856 11/1986 European Pat. Off. ..

Primary Examiner—Anthony McFarlane
Assistant Examiner—Nhat Phan
Attorney, Agent, or Firm—Armstrong, Nikaido, Marmelstein, Kubovcik & Murray

[57] ABSTRACT

The aromatic hydrocarbons rich in benzene, toluene and xylene are prepared from a hydrocarbon feed having from 6 to 12 carbon atoms by feeding the hydrogen in admixture with hydrogen in a ratio ranging from 0 to less than 1 mole with respect to each mole of the hydrocarbon, into contact with a catalyst prepared by depositing at least one metal belonging to group VIII of the periodic table on a macroporous zeolite treated with a halogenated compound. The aromatic hydrocarbons rich in benzene, toluene and xylene are useful as a base for high octane number gasoline or as petrochemical raw materials.

9 Claims, No Drawings

PROCESS FOR PREPARING AROMATIC HYDROCARBONS

BACKGROUND OF THE INVENTION

1. Field of the Invention

The present invention relates to a process for preparing aromatic hydrocarbons and, more particularly, to a process for efficiently preparing hydrocarbons rich in benzene, toluene, xylene and so on, useful for a base material of high octane number gasoline or for petrochemical raw materials, from hydrocarbons having from 6 to 12 carbon atoms.

2. Description of Related Art

As naphtha containing more volatile hydrocarbons, particularly light naphtha, has a limited field of uses, demands have been made to develop technology of efficiently converting the naphtha into aromatic hydrocarbons having a high content of benzene, toluene, xylene and so on, which have more value than the naphtha. Likewise, it is considered to be desirable to provide improved technology for reforming a variety of comparably lighter non-aromatic hydrocarbon fractions including light naphtha and gasoline fractions, into aromatic hydrocarbons rich in benzene, toluene and xylene.

Representative of a process for reforming naphtha using a platinum-deposited catalyst is a process for reforming non-aromatic hydrocarbons into aromatic hydrocarbons. Heretofore, however, a large amount of hydrogen has been supplied to the reaction system, together with a raw material for the reaction, in order to lengthen the life of the catalyst. Unless hydrogen is charged in a large amount, coke may deposit causing deactivation of the catalyst.

This process is effective to prevent deactivation of the catalyst to be used, however it suffers from the disadvantages that hydrogen to be used in a large amount is relatively expensive and hydrogenolysis of the hydrocarbon to be used is likely to occur, thereby incurring the risk of reducing selectivity to useful aromatic compounds.

In order to maintain catalytic activity and provide highly improved selectivity to useful aromatic compounds, for example, U.S. Pat. No. 4,416,806 proposes a catalyst with a metal belonging to the group VIII of the periodic table, such as platinum, deposited on a so-called macroporous zeolite such as an L-type zeolite or the like.

As is apparent from the examples of this U.S. Pat. No. 4,416,806, the catalyst used therein also requires hydrogen at a ratio to hydrocarbons of 0.2 to 1 in order to improve selectivity and extend the life of the catalyst. It is to be noted, however, that although the catalyst proposed in this prior patent publication is claimed to be an extended life catalyst, the yield of the aromatic hydrocarbons when using this catalyst is reduced from 38% to 23% as the process time is extended from 5 hours to 77 hours. Hence, the life of catalyst to this extent cannot be said to be sufficiently long from the viewpoint of an industrially available process.

In order to use the catalyst on an industrial basis, the catalyst is required to have a life extended to a sufficiently long period of time and yet to provide a sufficiently high selectivity to useful aromatic hydrocarbons.

SUMMARY OF THE INVENTION

Therefore, the present invention has the object to provide a process for economically and efficiently preparing aromatic hydrocarbons with high selectivity in the presence of a catalyst with a long life.

We have extensively studied improvements in the life of catalyst with a metal belonging to the group VIII of the periodic table, such as platinum or the like, deposited on a carrier such as an L-type zeolite or the like. As a result, many proposals have been made to processes for preparing hydrocarbons by reforming naphtha or the like using such a catalyst as have been treated with a halogenated compound, particularly with Fron, in various ways so as to have its life of catalyst extended, as disclosed for example in Japanese Patent Unexamined Publication (kokai) Nos. 57,653/1987, 11,985/1988, 91,334/1988, 75,350/1990, 23,194/1989 and 127,043/1989.

In the course of research, surprisingly, it has been found that the catalyst treated with Fron provides a longer life of catalyst as the ratio of hydrogen to hydrocarbon used during reforming becomes lower. The catalyst has also been found to provide improved selectivity to aromatic hydrocarbons and to act at reduced temperature, thereby proceeding readily with the reaction for the conversion of a suitable feed into the aromatic hydrocarbons. The present invention has been completed on the basis of this finding.

In order to achieve this object, the present invention consists of a process for preparing aromatic hydrocarbons, comprising contacting a less aromatic hydrocarbon, having from 6 to 12 carbon atoms, and hydrogen, in an amount less than 1 mole per mole of the hydrocarbon, with a catalyst comprising a metal belonging to group VIII of the periodic table, a macroporous zeolite and a halogen.

DESCRIPTION OF THE PREFERRED EMBODIMENTS

The present invention will be described more in detail by way of examples.

Catalyst

The catalyst to be used for the process according to the present invention comprises at least one of the metals selected from the metals of group VIII of the periodic table, a macroporous zeolite and a halogen.

a) Macroporous Zeolite

As the macroporous zeolite, an L-type zeolite is preferred, and a variety of zeolites such as X-type and y-type zeolites may optionally be used.

These macroporous zeolites may be used singly or in combination of two or more. A carrier such as other zeolites, silica-alumina, alumina, silica or other oxide or a binder may be used appropriately in combination with the macroporous zeolite as long as it does not adversely affect the object of the present invention.

The L-type zeolite to be used for the present invention may generally be represented by the following formula:

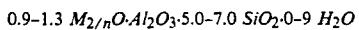

(wherein
M is an alkali metal or an alkaline earth metal; and
n is a valence of M).

Specifically, the L-type zeolite may be as is mentioned, for example, on pages 9 and 10 in Japanese Patent Unexamined Publication (kokai) No. 133,835/1983 and on page 5 in Japanese Patent Unexamined Publication (kokai) No. 80,333/1984. Hence, these patent publications are incorporated by reference in this specification.

b) Treatment with Halogenated Compound

For the catalyst to be used for the process according to the present invention, it is preferred to use the macroporous zeolite treated with the halogenated compound.

As the halogenated compound, a fluorinated compound is preferred, although a chlorinated compound, a brominated compound and an iodinated compound may be used.

The fluorinated compound may include, for example, a fluorinated hydrocarbon, called Fron gas, or a fluorinated chlorinated hydrocarbon, such as:

trichloromonofluoromethane $(CFCl_3)$(Fron 11)
dichlorodifluoromethane $(CF_2Cl_2)$(Fron 12)
monochlorotrifluoromethane $(CF_3Cl)$(Fron 13)
dichloromonofluoromethane $(CHFCl_2)$(Fron 21)
monochlorodifluoromethane $(CHF_2Cl)$(Fron 22)
trifluoromethane $(CHF_3)$(Fron 23)
tetrafluoromethane $(CF_4)$(Fron 14)
1,1,2-trichloro-1,2,2-trifluoroethane $(CFCl_2CF_2Cl)$ (Fron 113) or
1,2-dichloro-1,1,2,2-tetrafluoroethane $(CF_2ClCF_2Cl)$ (Fron 114).

As the halogenated compound other than the fluorinated compound, a chlorinated hydrocarbon may include, for example, tetrachloromethane $(CCl_4)$, chloroform $(CHCl_3)$, dichloromethane $(CH_2Cl_2)$, hexachloroethane $(C_2Cl_6)$, tetrachloroethane $(C_2H_2Cl_4)$ or dichloroethane $(C_2H_4Cl_2)$.

The treatment with the halogenated compound may be carried out prior to or subsequent to the deposition of the metal belonging to group VIII of the Periodic Table on the macroporous zeolite. The halogenated compound may be used in a mixture with gases, such as nitrogen, hydrogen or a mixture of nitrogen with hydrogen.

The conditions under which the macroporous zeolite is treated with the halogenated compound are not restricted to particular ones and may appropriately be determined in accordance with various situations. The macroporous zeolite may be contacted with the halogenated compound at a temperature ranging from 300° C. to 550° C., preferably from 450° C. to 550° C., for a time period ranging from 1 to 40 hours. The conditions for bringing the macroporous zeolite into contact with the halogenated compound may appropriately be determined in accordance with the kind and the concentration of the halogenated compound.

c) Deposition of Metal of Group VIII of Periodic Table

The catalyst to be used for the process according to the present invention may be prepared by depositing at least one metal of the group VIII of the periodic table on the macroporous zeolite.

The metal of the group VIII of the periodic table may include, for example, platinum, palladium, nickel, rhodium or the like. Among those metals, platinum is preferred.

As a source of platinum, a variety of sources may be used and they may specifically include, for example, a halogenated platinic acid such as chloroplatinic acid, bromoplatinic acid and iodoplatinic acid, a halogenated platinate such as sodium chloroplatinate, an ammine platinum complex salt such as tetraammineplatinum chloride, tetraammineplatinum hydroxide and dinitrodiaminoplatinum. In addition to those as described hereinabove, a nitrile platinum complex, a nitrosyl platinum complex, a phosphine platinum complex and an acetylacetonatoplatinum complex may also be used. Among the sources of platinum, the amine platinum complex and the halogenated platinic acid are preferred, and the amine platinum complex is more preferred. The sources of platinum may be used singly or in combinations of two or more.

A variety of sources of palladium may be used, and such sources of palladium may include, for example, a palladium halide such as palladium chloride, palladium nitrate, tetraamminepalladium chloride, ammonium tetrachloropalladate, palladium oxide palladium hydroxide, and so on. Among the sources of palladium, the palladium halide is preferred, and palladium chloride is particularly preferred. The sources of palladium may be used singly or in combination of two or more.

There may be used a variety of sources of nickel, and such sources of nickel may include, for example, a nickel halide such as nickel chloride, nickel bromide and nickel iodide, nickel nitrate, nickel sulfate, nickel hydroxide, nickel carbonate, nickel oxide, nickel acetate, nickel formate, nickel oxalate, acetylacetonatonickel, and so on. Among the sources of nickel, the nickel halide is preferred, and nickel chloride is particularly preferred. The sources of nickel may be used singly or in combinations of two or more.

A variety of sources of rhodium may be used, and such sources of rhodium may include, for example, a rhodium halide such as rhodium chloride, a halogenated rhodate such as sodium chlororhodate, an ammonium halorhodate such as ammonium chlororhodate, rhodium hydroxide, rhodium oxide, rhodium nitrate and so on. The rhodium halide is preferred, and rhodium chloride is specifically preferred. The sources of rhodium may be used singly or in combination of two or more.

The amount of the metal of group VIII of the periodic table to be deposited on the carrier may range usually from 0.1% to 5.0% by weight, preferably from 0.3% to 1.5% by weight, with respect to the weight of the catalyst.

The procedure of depositing the metal of group VIII of the periodic table on the carrier may include the usual wet deposition methods such as impregnation, e.g., vacuum impregnation or impregnation at ambient pressure, immersion, ion exchange, or solvent evaporation.

d) Miscellaneous

The shape of the catalyst to be used for the present invention is not restricted to a particular one, and a catalyst in various shapes may be used as desired. In forming the catalyst, an appropriate binder may be used. As long as the object of the present invention is not adversely affected, any binder may be used and such a binder may specifically include, for example, alumina, silica, silica-alumina and other clay minerals.

And other additives may be added as long as they do not impair the object of the present invention.

Raw Material

As the raw material for the preparation of the aromatic hydrocarbons according to the process of the present invention, there may be used hydrocarbon fractions having from 6 to 12 carbon atoms, which may be a linear, branched or cyclic paraffin-series hydrocarbon, a linear, branched or cyclic olefin-series hydrocarbon, and a linear, branched or cyclic acetylene-series hydrocarbon. The hydrocarbons as described hereinabove may be used singly or in combination of two or more, and more volatile hydrocarbon fractions or relatively volatile hydrocarbon fractions containing the hydrocarbons as described hereinabove as a main ingredient may also be used as the raw material for the process according to the present invention.

The linear or branched paraffin-series hydrocarbon may preferably include a paraffin-series hydrocarbon having from 6 to 10 carbon atoms, such as n-hexane, methylpentane, n-heptane, methylhexane, dimethylpentane, n-octane and so on.

The cyclic paraffin-series hydrocarbon may preferably include a paraffin-series hydrocarbon having from 6 to 10 carbon atoms, such as methylcyclopentane, cyclohexane, dimethylcyclohexane and so on.

The linear or branched olefin-series hydrocarbon may preferably include an olefin-series hydrocarbon having from 6 to 10 carbon atoms, such as hexene, methylpentene, heptene, methylhexene, octene and so on.

The cyclic olefin-series hydrocarbon may preferably include an olefin-series hydrocarbon having from 6 to 10 carbon atoms, such as methylcyclopentene, cyclohexene, methylcyclohexene, dimethylcyclohexene and so on.

The acetylene-series hydrocarbon may preferably include an acetylene-series hydrocarbon having from 6 to 10 carbon atoms, such as hexyne, heptyne, octyne and so on.

The raw material for the preparation of the aromatic hydrocarbons may contain impurities such as a monocyclic aromatic compound and methane if the object of the present invention is not affected adversely.

Condition of Process

In accordance with the process of the present invention, the aromatic hydrocarbons may be prepared by contacting an appropriate amount of the hydrocarbon having from 6 to 12 carbon atoms and a particular amount of hydrogen, to be optionally added, with the catalyst obtained by depositing at least one metal of group VIII of the periodic table on a macroporous zeolite treated with a halogenated compound. The above particular amount of hydrogen contains 0 mol per mole of the hydrocarbon fed.

The reaction for reforming the hydrocarbon into the aromatic hydrocarbons may be carried out in a reaction tower which is filled with the catalyst. The catalyst may be of fluidized bed, moving bed or fixed bed.

The amount of hydrogen to be optionally fed to the reaction system may be less than 1 mole per mole of the hydrocarbon to be used as the raw material and may preferably range from 0 to 0.5 mole per mole of the hydrocarbon.

If the amount of the hydrogen is larger than 1 mole, the life of catalyst cannot be improved to a sufficient extent and it is difficult to improve the yield of the aromatic hydrocarbons such as benzene, toluene, xylene and so on, or to lower the reaction temperature, thereby not achieving the object of the present invention.

The reaction pressure at which the reaction is carried out may range usually from ambient temperature to 40 kg/cm$^2$, preferably from ambient temperature to 10 kg/cm$^2$. The reaction temperature may be in the range usually from 350° C. to 600° C., preferably from 400° C. to 550° C. If the reaction temperature is too high, disadvantageous decomposition of the catalyst may occur, thereby reducing the yield of the aromatic hydrocarbons such as benzene, toluene and xylene or causing deactivation or destruction of the catalyst. If the reaction temperature is too low, the reaction velocity cannot be attained to a sufficient extent.

The reaction method is not restricted to a particular one and it may appropriately be selected from a continuous flow method, a semi-continuous flow method and a batch method. These methods may be used in combination with each other. The continuous flow method using a fixed bed of catalyst is preferred. The reaction may be of one stage reaction system although it may be of a multistage reaction system, such as of a two-stage reaction system.

When the reaction is carried out by the flow method, it is appropriate to supply the hydrocarbon as the raw material at a space velocity (WHSV) ranging usually from 0.1 to 20 hour$^{-1}$, preferably from 1 to 10 hour$^{-1}$.

The reaction may be carried out in the presence of an inert gas such as nitrogen gas, argon or helium as long as the presence of such an inert gas does not adversely affect the object of the present invention.

If the raw material, such as a hydrocarbon fraction having from 6 to 12 carbon atoms, contains a sulfur component it is preferred that the raw material is subjected to desulfurization in a conventional manner prior to the reaction, for example, by means of a desulfurizing tower disposed in front of the reaction tower. When the desulfurizing tower is so disposed, a portion or all of the hydrogen may be supplied to the desulfurizing reaction tower, together with the feed hydrocarbon having from 6 to 12 carbon atoms.

Under the conditions as described hereinabove, the process according to the present invention can convert a hydrocarbon fraction having from 6 to 12 carbon atoms into useful aromatic hydrocarbons, such as benzene, toluene, xylene and so on, with high yield and selectivity. Although the resulting reaction mixture contains benzene, toluene and xylene in large amounts, it also may contain other aromatic hydrocarbons, hydrogen and more volatile hydrocarbons, such as paraffins and olefins having from 1 to 5 carbon atoms.

The reaction mixture containing the aromatic hydrocarbons, such as benzene, toluene, xylene and so on, in large amounts may be treated by conventional separation methods such as vapor-liquid separation or evaporation, thereby appropriately separating gas fractions such as the more volatile hydrocarbons and hydrogen gas and heavy hydrocarbon fractions so as to produce hydrocarbons having a desired range of fractions, rich in benzene, toluene, xylene and so on, such as high octane number gasoline fractions and so on. Hydrogen by-produced during this reforming reaction may appropriately be recycled to the reaction tower or the desulfurizing reaction tower, thereby further improving efficiency in use of hydrogen.

The hydrocarbon fractions containing the useful aromatic hydrocarbons, such as benzene, toluene, xylene and so on, may be used as they are or after adjustment of components, purification or separation, as high octane number gasoline or its base, petrochemical raw material, solvents or the like.

As described hereinabove, the present invention can provide a process for efficiently and economically preparing useful aromatic hydrocarbons, such as benzene, toluene, xylene and so on, from feed hydrocarbons having from 6 to 12 carbon atoms. The process according to the present invention can lengthen the life of the catalyst by reforming the hydrocarbons using up to the particular amount of hydrogen in the presence of the particular catalyst, improve selectivity to the particular aromatic hydrocarbons, and lower the reaction temperature, thereby providing a process for preparing aromatic hydrocarbons rich in benzene, toluene, xylene and so on, which is highly advantageous on a practical scale.

The present invention will be described in more detail by way of examples with reference to comparative examples.

EXAMPLE 1

A quartz reaction tube having an inner diameter of 20 mm was filled with 15 grams of L-type zeolite (spherical; average diameter, 1.5 mm) formed with a silica binder and heated at 200° C. for 30 minutes while air was passing through the reaction tube. After air was shifted to Fron 13 ($CF_3Cl$), the reaction tube was heated to 500° C. and the reaction was continued at this temperature for 120 minutes. Thereafter, the gas was shifted to air again and the temperature was cooled down, thereby yielding L-type zeolite containing fluorine.

The resulting L-type zeolite was impregnated with an aqueous solution of tetraammineplatinum chloride in deionized water in an amount corresponding to the saturated water content of the L-type zeolite treated with Fron 13, so as to have platinum deposited thereon in a proportion of 1.0% by weight. After deposition of platinum, the resulting L-type zeolite was dried in a drier at 80° C. for 3 hours and then finely divided and passed through a sieve to thereby produce a catalyst having a size of 16 to 32 mesh.

A quartz reaction tube was filled with 1.5 grams of the catalyst and heated at 540° C. for 24 hours while passing hydrogen therethrough.

Then, the hydrocarbons having the composition as shown in Table 1 below, as raw materials, were supplied to the reaction tube filled with the catalyst at a space velocity (WHSV) of 2 hour$^{-1}$, together with hydrogen in a mole ratio of hydrogen to hydrocarbon ($H_2/HC$) of 0.5 to 1. The reaction was carried out under a pressure of 7 kg/cm$^2$ and the temperature was adjusted so as to allow the resulting aromatic hydrocarbons to have a concentration in the product hydrocarbons of 65% by weight at the outlet of the reaction tube. As a result, it was found that a reaction time period as long as 2,500 hours was required until the reaction temperature reached 525° C. The life of the catalyst was thus found to be very long.

Table 2 below shows reaction temperatures, compositions at the outlet of the reaction tube, and selectivities of the resulting aromatic hydrocarbons after 200 hours have elapsed after the start of the reaction.

EXAMPLE 2

The procedure of Example 1 was followed except for that no hydrogen was supplied. The reaction time period required as long as 3,000 hours until the reaction temperature reached 525° C., so that the life of catalyst was found to be very long.

Table 2 below shows the reaction temperatures, compositions at the outlet of the reaction tube, and selectivities of the resulting aromatic hydrocarbons after 200 hours have elapsed after the start of the reaction.

COMPARATIVE EXAMPLE 1

The procedure of Example 1 was followed except that the hydrogen was supplied in a ratio to the feed hydrocarbons of 2 to 1 and the amount of catalyst 0.5 gram. The reaction time period required as long as 2,000 hours until the reaction temperature reached 525° C.

Table 2 below shows the reaction temperatures, compositions at the outlet of the reaction tube, and selectivities of the resulting aromatic hydrocarbons after 200 hours have elapsed after the start of the reaction.

COMPARATIVE EXAMPLE 2

The procedure of Example 1 was followed except that the hydrogen was supplied in a ratio to the feed hydrocarbons of 5 to 1. The reaction time period required as long as 1,800 hours until the reaction temperature reached 525° C.

Table 2 below shows the reaction temperatures, compositions at the outlet of the reaction tube, and selectivities of the resulting aromatic hydrocarbons after 200 hours have elapsed after the start of the reaction.

TABLE 1

| Composition of Hydrocarbons (% by weight) | |
|---|---|
| 2,3-Dimethylbutane | 0.7 |
| 2-Methylpentane | 9.3 |
| 3-Methylpentane | 15.3 |
| n-Hexane | 59.7 |
| Methylcyclopentane | 13.5 |
| Others | 1.5 |

TABLE 2

| | Example 1 | Example 2 | Comparative Ex. 1 | Comparative Ex. 2 |
|---|---|---|---|---|
| Mole $H_2$/HC Ratio | 0.5/1 | 0 | 2/1 | 5/1 |
| Reaction Temp, °C. | 450 | 444 | 474 | 479 |
| $C_1$—$C_5$ Hydrocarbon (% by wt) | 5.6 | 4.8 | 9.6 | 10.8 |
| $C_6$ Non-Aromatic Hydrocarbon, % by wt | 28.5 | 30.4 | 26.2 | 23.8 |
| Aromatic Hydrocarbon % by wt | 65.9 | 64.8 | 64.2 | 65.4 |
| Selectivity to Aromatic Hydrocarbon, % by wt | 92.2 | 93.1 | 87.0 | 85.8 |

EXAMPLE 3

The procedure of Example 1 was followed except for the reaction pressure of 5 kg/cm$^2$. The reaction time period required as long as 3,100 hours until the reaction temperature reached 525° C.

Table 3 below shows the reaction temperatures, compositions at the outlet of the reaction tube, and selectivities of the resulting aromatic hydrocarbons after 100 hours have elapsed after the start of the reaction.

COMPARATIVE EXAMPLE 3

The procedure of Example 3 was followed except that the L-type zeolite was not treated with Fron 13. The reaction time period required as long as 160 hours until the reaction temperature reached 525° C.

Table 3 below shows the reaction temperatures, compositions at the outlet of the reaction tube, and selectivities of the resulting aromatic hydrocarbons after 100 hours have elapsed after the start of the reaction.

TABLE 3

|  | Example 3 | Comparative Ex. 3 |
| --- | --- | --- |
| Mole $H_2$/HC Ratio | 0.5/1 | 0.5/1 |
| Reaction Temp. °C. | 448 | 493 |
| $C_1$—$C_5$ Hydrocarbon (% by wt) | 5.4 | 6.8 |
| $C_6$ Non-Aromatic Hydrocarbon, % by wt | 30.6 | 29.6 |
| Aromatic Hydrocarbon % by wt | 64.0 | 63.6 |
| Selectivity to Aromatic Hydrocarbon, % by wt | 92.2 | 90.3 |

What is claimed is:

1. In a process for preparing aromatic hydrocarbons from a hydrocarbon having from 6 to 12 carbon atoms with the aid of a catalyst consisting essentially of at least one metal belonging to group VIII of the periodic table, a macroporous zeolite and a halogen, the improvement which comprises feeding the hydrocarbon having from 6 to 12 carbon atoms in admixture with hydrogen in a ratio with respect to a mole of the hydrocarbon ranging from 0 to less than 1 mole; and contacting said mixture with said catalyst.

2. A process as claimed in claim 1, wherein the metal belonging to group VIII of the periodic table is platinum.

3. A process as claimed in claim 1, wherein the metal belonging to group VIII of the periodic table is present in a proportion of 0.1% to 5.0% by weight with respect to weight of the catalyst.

4. A process as claimed in claim 1, wherein the macroporous zeolite is Zeolite L.

5. A process as claimed in claim 1, wherein the hydrocarbon having from 6 to 12 carbon atoms is contacted with the catalyst at a pressure ranging from ambient pressure to 40 kg/cm$^2$ and a temperature ranging from 400° C. to 550° C. by flowing the hydrocarbon at a weight hourly space velocity ranging from 0.1 to 20 hour$^{-1}$.

6. A process as claimed in claim 1 wherein said macroporous zeolite is Zeolite L.

7. A process as claimed in claim 1 wherein said hydrogen to hydrocarbon mole ratio is 0 to 0.5.

8. A process as claimed in claim 1 wherein said hydrogen to hydrocarbon mole ratio is 0.

9. A process as claimed in claim 6 wherein said hydrogen to hydrocarbon mole ratio is 0.

* * * * *